United States Patent [19]

Seed

[11] Patent Number: 5,726,293
[45] Date of Patent: Mar. 10, 1998

[54] AFFINITY PURIFICATION METHODS INVOLVING IMIDAZOLE ELUTION

[75] Inventor: Brian Seed, Boston, Mass.

[73] Assignee: The General Hospital Corporation, Boston, Mass.

[21] Appl. No.: 250,317

[22] Filed: May 27, 1994

Related U.S. Application Data

[63] Continuation of Ser. No. 956,902, Oct. 2, 1992, abandoned.

[51] Int. Cl.$^6$ .......................... C07K 13/22; C07K 16/00; C07K 16/46; C07D 233/54
[52] U.S. Cl. ...................... 530/413; 530/412; 530/387.1; 530/391.1; 548/335.1
[58] Field of Search .............................. 530/391.1, 387.1, 530/414, 412, 812, 413; 548/335

[56] References Cited

PUBLICATIONS

Aruffo et al, Cell 67:35–44, 1991.
Pytela et al (1985) Cell 40:191–198.
Harlow et al (1988) "Antibodies: A Laboratory Manual" ColdSpring Harbor Press, Cold Spring Harbor, pp. 514–552.
Stryer, L. (1988) "Biochemistry" W.H. Freeman & Co, N.Y. pp. 20–21.
"The Merck Index" (1976) M. Windholy et al (eds).. Merck & Co., Inc. Raherag, N.Y. p. 4811.
"Calbiochem Biochemicals for Research" Catalog (1990–1991) Calbiochem Corp, San Diego, CA p. 127.
Sjodahl, J. (1976) FEBS Lett. 67(1):62–67.
Shing, Y. (1988) J. Biol. Chem. 263(18):9059–9062.
Bush et al (1991) J. Biol Chem. 266(21):13811–13814.
Robbins et al (1987) Biochemistry 26:4661–4667.
Medici et al (1989) Biochemistry 28:212–219.

*Primary Examiner*—Paula K. Hutzell
*Assistant Examiner*—Jacqueline G. Krikorian
*Attorney, Agent, or Firm*—Clark & Elbing LLP

[57] ABSTRACT

Disclosed is a method of isolating a protein from a sample, involving (i) providing a first molecule which is capable of forming an affinity complex with the protein; (ii) contacting the sample with the first molecule under conditions which allow affinity complex formation; (iii) isolating the complex; (iv) treating the complex with imidazole to disrupt the complex, causing the release of the protein from the complex; and (v) isolating the protein. According to one embodiment, imidazole is used as a very gentle elution reagent to disrupt a protein A-antibody fusion protein complex, a technique which has general application for the isolation of antibodies or recombinant antibody fusion proteins.

8 Claims, 1 Drawing Sheet

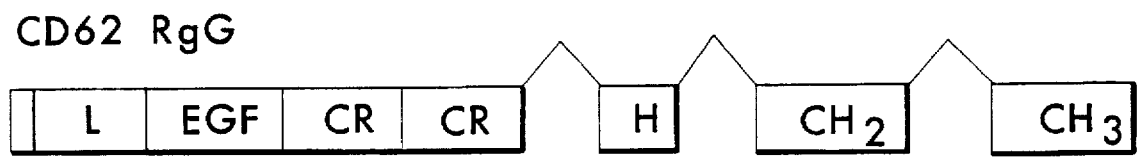
FIG. 1
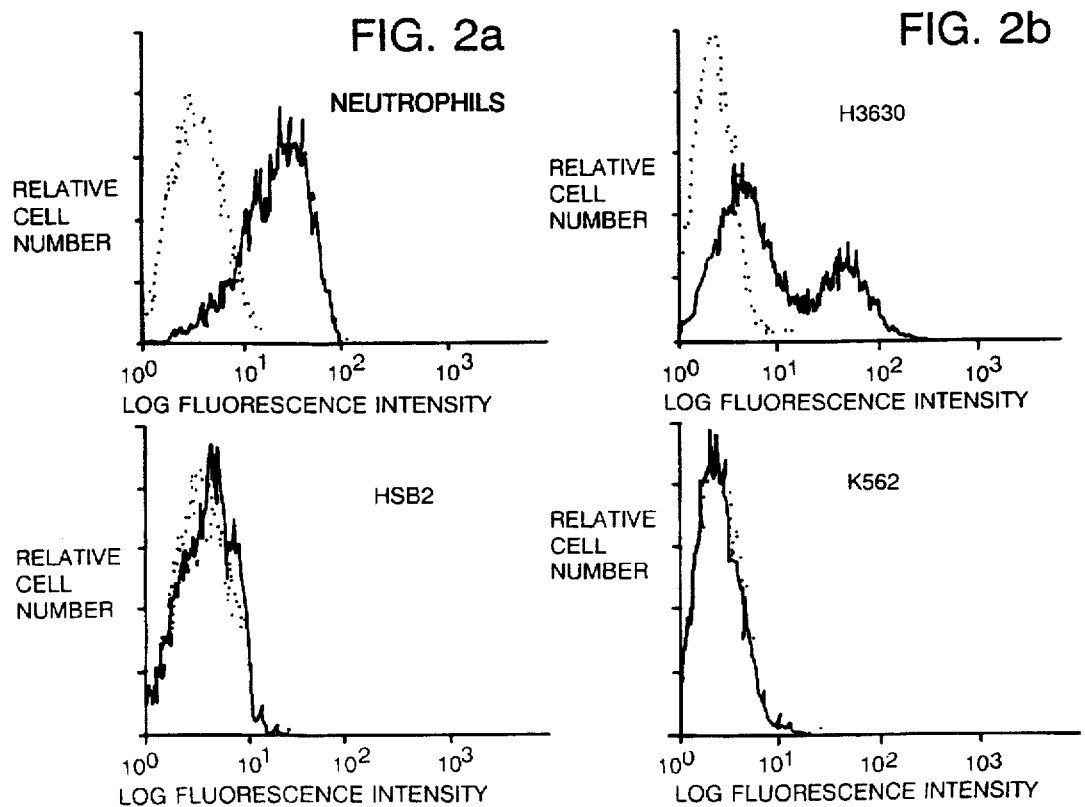

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 42
( B ) TYPE: nucleic acid
( C ) STRANDEDNESS: single
( D ) TOPOLOGY: linear ( x i ) SEQUENCE DESCRIPTION: SEQ ID NO: 1:

GGCGCCGAAG CTTCCATGGC CAACTGCCAA ATAGCCATCT TG           42

( 2 ) INFORMATION FOR SEQ ID NO: 2:

( i ) SEQUENCE CHARACTERISTICS:
( A ) LENGTH: 39
( B ) TYPE: nucleic acid
( C ) STRANDEDNESS: single
( D ) TOPOLOGY: linear ( x i ) SEQUENCE DESCRIPTION: SEQ ID NO: 2:

GGCCAGATCT CCCTGCACAG CTTTACACAC TGGGGCTGG           39

AFFINITY PURIFICATION METHODS INVOLVING IMIDAZOLE ELUTION

This application is a continuation of Ser. No. 07/956,902, filed Oct. 2, 1992, now abandoned.

This invention was made with Government support under Contract #AI27849 and DK43031 awarded by the National Institutes of Health. The Government has certain rights in this invention.

BACKGROUND OF THE INVENTION

The invention relates to protein isolation and purification techniques.

There currently exists a variety of methods, materials, and approaches for the separation of a particular protein from the other components of a biological sample. One general approach exploits the non-specific affinity of a protein for a substrate. For example, proteins may be separated based upon their molecular charge using ion exchange chromatography, whereby protein mixtures are applied to an oppositely charged, chromatographic matrix, and the various proteins bind to the matrix by reversible, electrostatic interactions. The adsorbed proteins are eluted, in order of least to most strongly bound, by increasing the ionic strength or by varying the pH of the elution buffer.

Another general approach makes use of a protein's physical characteristics as a means of separation. For example, a protein may be separated based upon its size, using gel filtration. By this method, protein mixtures are applied to a gel-filtration column containing a chromatographic matrix of defined pore size. Proteins are eluted, generally with an aqueous buffer, collected as individual chromatographic fractions and analyzed.

Finally, a third general approach makes use of the specific affinity of a protein for a purifying reagent. A protein, for example, may be purified using an antibody specific for that protein or conversely an antibody may be purified using its specific antigen. Typically, the antibody or antigen is bound to a column substrate and a solution which includes the particular antigen or antibody applied to the column, allowing immunocomplex formation. Bound immunocomplex partners are then eluted by destabilizing the antigen-antibody complex, e.g., by exposure to buffers of very high ionic strength or high or low pH. Alternatively, immunocomplex formation may be exploited to purify the antigen or antibody by immunoprecipitation. Antigen-antibody complexes may be precipitated following aggregation, or alternatively, one of the binding partners may be covalently linked to a solid particle (such as Sepharose or agarose) and immunoaffinity complexes isolated by centrifugation. In either method, the protein of interest is then released from the complex, again, e.g., by exposure to buffers of high ionic strength or high or low pH.

Of particular interest to molecular biologists are isolation and purification methods for antibodies or recombinant antibody fusion proteins. Structurally, an individual antibody molecule includes two identical heavy (H) chains and two identical light (L) chains; each light chain is disulfide bonded to a heavy chain, and the heavy chains are disulfide bonded to each other to form the basic dimeric structure of the molecule. Within each chain, units made up of about 110 amino acids fold up to form compact domains, themselves held together by a single internal disulfide bond. The L chain has two domains, and the H chains have four or five domains.

The first two N-terminal domains of the H chains interact with the two L chain domains, producing the "Fab domain", a portion of the molecule which directs specific antigen recognition and binding. At the other end of the molecule, the extreme C-terminal domains of the H chains (termed the $C_H2$ and $C_H3$ domains) interact to produce the "Fc domain", a portion of the molecule which directs a number of immunoglobulin functions including binding to cells, fixing complement, and traversing the placenta. And, finally, lying between the Fab and Fc domains are a small number of amino acids which make up the hinge region, a flexible domain facilitating free movement of the antigen binding portion of the molecule.

SUMMARY OF THE INVENTION

It is an object of the invention to provide a cheap and general method for eluting proteins adsorbed to affinity chromatography columns.

As discussed generally above, affinity chromatography is a highly effective method for purifying proteins which exploits specific interactions between the proteins to be purified and a solid phase immobilized ligand. Typically the solid phase ligand has some unique chemical character which results in the selective adsorption of the protein of interest. Contaminant proteins either do not bind the solid phase or can be removed by washing the solid phase with appropriate solutions. Historically, elution of an affinity column has been accomplished by either of two methods: (i) washing the matrix with a solution of specific ligand resembling the immobilized ligand, or (ii) washing the matrix with solutions of very high ionic strength, or very high (>11) or very low (<3) pH. In general, method (i) is more attractive than method (ii) because solutions of very high ionic strength, while usually not deleterious to proteins, are also usually not effective at desorbing proteins which bind to the affinity matrix tightly, and many proteins are labile to buffers sufficiently acid or basic to elute the protein of interest. However method (i) is not applicable if a specific eluting ligand can not be found or if the use of a specific eluting ligand is infeasible for practical reasons, e.g. if the specific ligand is unstable or expensive.

Elution of proteins from immobilized ligands in which the ligand itself is a protein can rarely be achieved by the use of an eluting solution containing a specific ligand. This is because the specific ligand usually must be a protein or peptide fragment, and elution is then infeasible for the practical reasons mentioned above.

The instant invention describes a new method for eluting proteins from affinity matrices based on the ability of the compound imidazole to act as a mild denaturant which disrupts protein interactions and thereby facilitates the release of proteins bound to affinity ligands.

Accordingly, in general, the invention features a method of isolating a protein from a sample, involving (i) providing a first molecule which is capable of forming an affinity complex with the protein; (ii) contacting the sample with the first molecule under conditions which allow affinity complex formation; (iii) isolating the complex; (iv) treating the complex with imidazole to disrupt the complex, causing the release of the protein from the complex; and (v) isolating the protein.

In a preferred embodiment, the first molecule is protein A and the protein to be isolated is an antibody or an antibody fusion protein which includes a protein A-binding domain.

In other preferred embodiments, the first molecule is an antibody and the protein to be isolated is a recombinant protein; or the first molecule is an antigenic protein and the protein to be isolated is an antibody which specifically binds that antigenic protein.

By "antibody fusion protein" is meant a protein which includes at least a portion of an immunoglobulin Fc domain directly or indirectly covalently bonded to a non-immunoglobulin polypeptide.

By "protein A-binding domain" is meant that portion of the immunoglobulin molecule which interacts with the *Staphylococcus aureus* cell wall component termed protein A. By crystallographic studies, this domain is most likely positioned at the $C_H2/C_H3$ cleft.

Applicant has recognized that affinity purification techniques may be modified such that imidazole is used as an elution reagent in the final step of purification to release the protein of interest from the affinity complex. Because this approach is considerably gentler than more conventional elution techniques (e.g., elution steps based on changes in solution pH), applicant's method facilitates the isolation and purification of those proteins which are destroyed (e.g., irreversibly denatured) or reduced in activity by standard elution procedures. Moreover, because imidazole represents a convenient and inexpensive elution reagent, it may be utilized as an alternative elution reagent even for the purification of more stable proteins.

Other features and advantages of the invention will be apparent from the following description of the preferred embodiments, and from the claims.

BRIEF DESCRIPTION OF THE DRAWINGS

FIG. 1 shows a schematic of the immunoglobulin fusion protein CD62 Rg.

FIGS. 2A, 2B, 2C, and 2D show flow cytometric results which indicate that CD62 Rg binds to the surface of myeloid and certain tumor cells.

DETAILED DESCRIPTION

There now follows a description of a protein isolation and purification procedure according to the invention, and a description of its use in the isolation of one particular immunoglobulin fusion protein. Unusually gentle elution of the recombinant protein facilitates purification without appreciable loss of native binding reactivity. This example is provided for the purpose of illustrating, not limiting, the invention.

Affinity Purification of IgG1 by Imidazole Elution

Human IgG1 was purified by affinity chromatography followed by imidazole elution as follows.

Human IgG1 was loaded on protein A trisacryl beads (Pierce, Rockford, Ill.), and washed with phosphate buffered saline. The beads were divided among several small columns, and the columns were eluted with solutions containing imidazole at 1, 2, 3, 4, or 5M concentration, adjusted to a final pH of 6, 7, 8, or 9. The results are given in Table 1 as the percent of maximum elution obtained for any one pH.

TABLE 1

| Imidazole | Fraction Eluted* | | | |
|---|---|---|---|---|
| [M] | pH 9 | pH 8 | pH 7 | pH 6 |
| 1.00 | 0.59 ± 0.03 | 0.54 ± 0.02 | 0.58 ± 0.06 | 0.49 ± 0.03 |
| 2.00 | 0.69 ± 0.13 | 0.80 ± 0.04 | 0.80 ± 0.03 | 0.76 ± 0.01 |
| 3.00 | 0.78 ± 0.26 | 0.83 ± 0.04 | 0.93 ± 0.00 | 0.86 ± 0.01 |

TABLE 1-continued

| Imidazole | Fraction Eluted* | | | |
|---|---|---|---|---|
| [M] | pH 9 | pH 8 | pH 7 | pH 6 |
| 4.00 | 0.94 ± 0.14 | 1.00 ± 0.05 | 1.00 ± 0.00 | 0.91 ± 0.04 |
| 5.00 | 1.00 ± 0.08 | 0.96 ± 0.01 | 0.93 ± 0.07 | 1.00 ± 0.03 |

*Mean ± std. error

Negligible amounts of IgG1 were retained by the columns at the highest imidazole concentrations, at any pH. In general the pH did not play a significant role in mediating the elution power of imidazole, which was somewhat unexpected, given that the pK of imidazole is 7.1, and so approximately 90% of the molecules would be charged at pH 6, whereas approximately 90% would be uncharged at pH 8.

Using this method, immunoglobulin fusion proteins, as well as IgG1 alone, were purified from protein A columns without loss of biological activity of the protein moiety fused to the immunoglobulin constant domain (in particular, see the purification of CD62 Rg below). For several of the fusion proteins purified in this manner, it was known that acidic elution conditions destroyed the activity (i.e., the ligand binding activity) known to reside in the portion of the protein fused to the immunoglobulin domain. In general, the purification of these immunoglobulin fusion proteins involved an initial isolation of a crude preparation of a fusion protein (including the hinge, $C_H2$ and $C_H3$ domains of human IgG1 joined to the extracellular domain of some surface antigen) which had been prepared by transfection of COS cells with the appropriate cDNA constructs. Media supernatants were collected from transfected cells which had been grown for a further 5 to 10 days, clarified by centrifugation, and adsorbed to protein A trisacryl or protein A agarose beads. The beads were collected, washed thoroughly with phosphate buffered saline containing 1% nonionic detergent (Nonidet P40 or Triton X-100) followed by buffer alone, then eluted with 4M imidazole adjusted to pH 8 with acetic or hydrochloric acids. The eluted fusion proteins were dialyzed against buffer, or the imidazole was removed by two cycles of centrifugal ultrafiltration (Centricon 30, Amicon Corp., Beverly, Mass.).

One particular example of such an antibody fusion protein purification now follows.

Isolation of a Soluble CD62: Immunoglobulin Fusion Protein

CD62 protein chimeras were prepared by genetic fusion of the first four N-terminal extracellular domains of CD62 to the hinge domain of human IgG1 as follows. CD62 cDNA sequences encoding the lectin (L), epidermal growth factor (EGF), and first two complement regulatory protein repeat elements (CR) were amplified in polymerase chain reactions using synthetic oligonucleotides designed to allow fusion to the human IgG1 artificial splice donor sequences described previously (Aruffo et al., Cell 61, 1303–1313, 1990) (FIG. 1). The forward primer bore the sequence GGC GCC GAA GCT TCC ATG GCC AAC TGC CAA ATA GCC ATC TTG (SEQ ID NO:1), while the reverse primer bore the sequence GGC CAG ATC TCC CTG CAC AGC TTT ACA CAC TGG GGC TGG (SEQ ID NO:2); the sequence allowed the CD62 fragment to be inserted as a HindIII to BglII fragment into HindIII- and BamHI-digested vector. To amplify the DNA, 20 PCR cycles were conducted, consisting of 30 s at 94° C., 2 min at 45° C., and 3 min at 72° C., using the reaction buffer recommended by the enzyme vendors (US Biochemical, Cleveland, Ohio), and MluI-digested DNA prepared from a previously described endothelial cell expression library (Bevilacqua et al., Science 243, 1160–1165, 1989). A schematic of the resultant fusion protein, termed CD62 Rg, is shown in FIG. 1.

The CD62 Rg expression plasmid was transfected into COS cells using DEAE dextran as previously described (Seed and Aruffo, Proc. Natl. Acad. Sci. USA 84:3365–3369, 1987); typically, ten 100 mm semiconfluent plates of COS cells were transfected with each construct. Twelve hours following transfection, cells were trypsinized, seeded onto fresh 100 mm dishes, and allowed to grow for 7–10 days. On the fourth day, 5 ml of fresh media/10% calf serum was added per dish. Supernatants were harvested, centrifuged to remove nonadherent cells and debris, pooled, and stored at 4° C. Gel electrophoresis of such supernatants demonstrated that the expression plasmids encoded the recombinant globulins and that these globulins appeared in soluble form in the supernatants of the transfected COS cells.

Initial attempts to purify the CD62 Rg fusion proteins by chromatography on protein A columns were hampered by the lability of the fusion proteins to the acidic buffers typically used to elute immunoglobulins. To circumvent this problem, applicants eluted instead with a solution of imidazole. 4M imidazole proved to be a mild and effective eluant, allowing retention of carbohydrate and tissue reactivity (see below).

This imidazole purification procedure was carried out as follows. Twelve hours following transfection, a fraction of the COS cells transfected with each construct were seeded onto flasks. Thirty-six hours post-transfection, the cells were washed with phosphate-buffered saline (PBS) and overlayed with cysteine-methionine-free media for 30 min. [$^{35}$S]-methionine and [$^{35}$S]-cysteine (TransLabel, ICN, Costa Mesa, Calif.) were added to a final concentration of 150 µCi/ml, and the cells were allowed to incorporate the label overnight. The supernatants were harvested and incubated with 200 µl of protein A Trisacryl (Pierce, Rockford, Ill.) at 4° C. for 12 hr. The beads were collected by centrifugation and washed with PBS/1% Nonidet P-40. For analysis, the beads were eluted with 200 µl of 1% sodium dodecyl sulfate. Ten microliters of each eluate was loaded on a 6% discontinuous polyacrylamide gel with or without prior exposure to mercaptoethanol. For preparative elution, columns were washed with 5 bed volumes of 4M imidazole (pH 8) (neutralized with acetic acid). Eluted proteins were stored for short periods of time in imidazole at 4° C. or 8° C., or exchanged into PBS by centrifugal ultrafiltration for longer term storage.

CD62 Rg Tissue Reactivity

To test the purified protein's ability to react with cells and tissues in a manner characteristic of CD62, the following binding assays were performed on myeloid and tumor cell lines, i.e., cells normally bound by native CD62.

Typically, $10^6$ cells were incubated with undiluted Rg supernatants for 30 min on ice in the presence of 10% rabbit serum. Cells were washed once with PBS and exposed to fluorescein-conjugated goat antibodies to human IgG or IgM (Cappel, Malver, Pa.) at a concentration of 1 to 5 µg/ml for 30 min on ice, followed by fixation in PBS containing 4% formaldehyde. Fluorescence profiles were determined by standard techniques with a FACScan analyzer. Results are shown in FIG. 2; solid lines indicate reactivity with CD62 Rg, and dotted lines indicate reactivity with control CD7 Rg protein.

Flow cytometry and fluorescence microscopy showed that CD62 Rg reacted with a cell surface ligand on freshly isolated human granulocytes, on the breast carcinoma cell lines H3630 and H3396, and on the myeloid cell lines HL60, THP-1, and U937 (FIGS. 2A and 2B). Cell surface reactivity was not found with the leukemic T cell lines HSB-2, Jurkat, or HPB-ALL, with K562 (erythroleukemia) cells, HeLa cells, COS cells, RD (rhabdomyosarcoma) cells, H3606 and H3620 melanoma cells, or the L tk$^-$ and NIH 3T3 murine fibroblast cells lines (FIGS. 2C and 2D). Control immunoglobulin fusion proteins CD7 Rg and CD8 Rg, and native IgG, did not show appreciable reactivity under these conditions (FIGS. 2A, 2B, 2C, and 2D). In many cases, the amount of CD62 Rg bound to permeabilized cells greatly exceeded the amount bound to unpermeabilized cells, suggesting that substantial internal stores were present.

CD62 Rg Carbohydrate Reactivity

Because glycolipids frequently express complex carbohydrate determinants in lineage-restricted developmental patterns, we investigated whether lipid extracts of HL60 cells (a promyelocytic leukemia line) would bind to CD62 Rg in either soluble or adsorbed form. The upper and lower phases of a Folch partition of HL60 cells was subjected to thin layer chromatography on silica gel plates, and the chromatograms were incubated with radiolabeled CD62 or control fusion proteins, washed, and subjected to fluorograph as follows.

Cells ($1 \times 10^8$ to $5 \times 10^8$) were extracted by homogenization with 20 vol of a 2:1 chloroform:methanol solution. The crude extract was filtered through lipid-free filter paper and subjected to repeated Folch partitions as described (Hakomori and Siddiqui, Meth. Enzymol. 32:345–367, 1974). Both upper and lower phases were evaporated and subsequently dissolved in 200 µl of methanol. Lipids from culture supernatants were extracted (1:1 v/v) with butanol saturated with 1M NaCl. The butanol phase was dried by evaporation and the residue resuspended in methanol.

Aluminum-backed silica gel HPTLC plates (5 cm×7.5 cm) (E. Merck, Darmstadt) were used for chromatography, and glycolipids were separated in chloroform/methanol/water (120/70/14). After chromatography, plates were dried, fixed by immersion in 0.1% polisobutylmethacrylate in hexane (Magnani et al., Meth. Enzymol. 83:235–241, 1982), and incubated for 1 hr at 22° C. in blocking solution (150 mM NaCl, 3 mM CaCl$_2$, 2% BSA). $^{35}$S-labeled Rg ($1 \times 10^5$ to $2 \times 10^5$ cpm/ml), i.e., either CD62 Rg or control fusion protein ELAM-1 Rg, was added and allowed to incubate with the plates overnight. The chromatograms were then washed twice for 30 min each in 150 mM NaCl, 3 mM CaCl$_2$, dried, sprayed with En$^3$Hance, and subjected to fluorography.

Glycolipids migrating either as a single band or, in different solvent systems, as a closely spaced doublet, were found to react strongly with CD62 Rg. No reactivity was detected in ganglioside fractions under these or more potently eluting conditions.

Parallel evaluation of the chromatographic pattern of different purified glycolipids indicated that the HL60 lipids comigrated in three different solvent systems [specifically, chloroform/methanol/water (120/70/14), chloroform/methanol/water (73/21/4), and chloroform/methanol/ acetone/acetic acid/water (10/2/4/2/1) (Ishizuka et al., J. Biol. Chem. 253:898–907, 1978)] with commercial preparations of bovine brain sulfatides (Sigma, St. Louis, Mo.; Matreya, Bellefonte, Pa.), 3-sulfated galactosyl ceramides bearing heterogenous fatty acyl substitution on the 2-amino position of the sphingosine moiety.

Chromatography and analysis of the purified glycolipids under the same conditions (i.e., two micrograms (by dry mass) of each of the lipid standards: either brain gangliosides (Sigma, St. Louis, Mo.; Matreya, Bellefonte, Pa.), sulfatides (Sigma, St. Louis, Mo.; Matreya, Bellefonte, Pa.), trisialyl ganglioside GT1b (Sigma, St. Louis, Mo.), galactosyl ceramides with hydroxyl substitution (Sigma, St. Louis, Mo.), or lysosulfatide (Sigma, St. Louis, Mo.; Matreya, Bellefonte, Pa.) reacted with CD62 Rg or control ELAM-1 Rg and developed with chloroform/methanol/water 73/21/4) confirmed that sulfatides reacted strongly with CD62, and that the more polar form was recognized preferentially under these conditions. Lysosulfatides, lacking the fatty acyl substitution, were not recognized, nor were galactosyl ceramides, lacking the sulfate residue, either with or without hydroxyl substitution on the fatty acid chain. Glycolipid bearing CD15 did not detectably react with CD62 Rg under conditions allowing detection of sulfatides. Neither CD7 Rg, CD8 Rg (Aruffo et al., Cell 61, 1303–1313, 1990), ELAM-1 Rg (Walz et al., Science 250:1132–1135, 1990), intact IgG1, or a COS cell preparation of a fragment of the IgG1 corresponding to the Fc fragment present in CD62 Rg reacted with sulfatides.

Other Embodiments

Applicant has recognized that affinity purification techniques may be modified such that imidazole is used in the final step of purification as an elution reagent to release the protein of interest from the affinity complex. Because imidazole acts as a non-specific mild denaturant, such an imidazole elution step may be employed in any standard affinity purification procedure (e.g., to release a protein from a column-bound complex or from a complex included in an immunoprecipitate) and may be used for the release of any immobilized protein.

What is claimed is:

1. A method of isolating an antibody or an antibody fusion protein from a sample, said antibody or said antibody fusion protein comprising a protein A-binding domain, said method comprising:
   (a) contacting said sample with protein A under conditions which allow affinity complex formation between said antibody or said antibody fusion protein and protein A;
   (b) separating the complex formed in step (a) from said sample;
   (c) treating said complex with imidazole in an amount sufficient to release said antibody or said antibody fusion protein from said complex; and
   (d) recovering said antibody or said antibody fusion protein.

2. The method of claim 1, wherein said antibody is IgG.

3. The method of claim 1, wherein said protein A-binding domain is from an IgG molecule.

4. The method of claim 1, wherein said antibody or said antibody fusion protein comprises a CH2 and a CH3 domain.

5. The method of claim 4, wherein said antibody or said antibody fusion protein further comprises a hinge domain.

6. The method of claim 1, wherein said imidazole is used at a concentration of between 1M and 5M inclusive.

7. The method of claim 6, wherein said imidazole is used at a concentration of 4M.

8. The method of claim 1, wherein said imidazole is used at between pH6 and pH9.

* * * * *